(12) United States Patent
Sunami et al.

(10) Patent No.: US 8,749,780 B2
(45) Date of Patent: Jun. 10, 2014

(54) CIRCULAR DICHROISM SPECTROMETER HAVING ALIGNMENT MECHANISM

(71) Applicant: JASCO Corporation, Hachioji (JP)

(72) Inventors: Tetsuji Sunami, Hachioji (JP); Jun Koshoubu, Hachioji (JP)

(73) Assignee: JASCO Corporation, Hachioji-shi, Tokyo (JP)

( * ) Notice: Subject to any disclaimer, the term of this patent is extended or adjusted under 35 U.S.C. 154(b) by 0 days.

(21) Appl. No.: 13/851,984

(22) Filed: Mar. 28, 2013

(65) Prior Publication Data

US 2013/0258334 A1    Oct. 3, 2013

(30) Foreign Application Priority Data

Mar. 29, 2012    (JP) ................................. 2012-075506

(51) Int. Cl.
- *G01J 3/28* (2006.01)
- *G01J 3/447* (2006.01)
- *G01J 3/02* (2006.01)

(52) U.S. Cl.
CPC ............... *G01J 3/447* (2013.01); *G01J 3/0208* (2013.01); *G01J 3/0237* (2013.01)
USPC ............................ 356/327; 356/326; 356/364

(58) Field of Classification Search
CPC ........ G01J 3/447; G01J 3/0208; G01J 3/0237
USPC ............................ 356/326, 327, 364–369, 491
See application file for complete search history.

(56) References Cited

U.S. PATENT DOCUMENTS

| | | | | |
|---|---|---|---|---|
| 5,708,504 A * | 1/1998 | Hopkins | ........................ | 356/456 |
| 5,788,632 A * | 8/1998 | Pezzaniti et al. | .............. | 600/316 |
| 6,480,277 B1 * | 11/2002 | Nafie | .............................. | 356/364 |
| 7,002,692 B2 * | 2/2006 | Akao et al. | ..................... | 356/491 |
| 2003/0234937 A1 | 12/2003 | Akao et al. | | |
| 2007/0222988 A1 * | 9/2007 | Jiang et al. | ..................... | 356/367 |
| 2009/0009859 A1 * | 1/2009 | Kawai et al. | ................... | 359/386 |

FOREIGN PATENT DOCUMENTS

JP    2004-020539    1/2004

* cited by examiner

*Primary Examiner* — Sang Nguyen
(74) *Attorney, Agent, or Firm* — Rankin, Hill & Clark LLP (57) ABSTRACT

A circular dichroism (CD) spectrometer includes an alignment mechanism that automatically adjusts the elements thereof at appropriate positions. The spectrometer has a focusing-lens position-and-orientation adjustment mechanism which adjusts the position and the orientation of the detector-side focusing lens. It also has a detector rotation mechanism which adjusts the orientation of the detector. Firstly, a control PC monitors the CD spectrum of D form of optical enantiomers, and the adjustment mechanism adjusts the focusing lens such that the monitored CD spectrum matches the reference spectrum related to the D form. Next, the control PC moniters CD spectrum of L form of optical enantiomers, and the adjustment mechanism adjusts the focusing lens such that the monitored CD spectrum of the D and L forms become symmetrical. And, the rotation mechanism adjusts the orientation of the detector such that the intensity of the detector signal is maximized.

12 Claims, 2 Drawing Sheets

CIRCULAR DICHROISM SPECTROMETER HAVING ALIGNMENT MECHANISM

CROSS-REFERENCE TO RELATED APPLICATIONS

This application is based on and claims the benefits of priority from Japanese Patent Application No. 2012-075506, filed on Mar. 29, 2012, the entire contents of which are incorporated herein by reference.

BACKGROUND OF THE INVENTION

1. Field of the Invention

The present invention relates to circular dichroism spectrometers, and more specifically, to alignment of optical positions of elements in a circular dichroism spectrometer.

2. Description of the Related Art

Two given molecules that consist of identical atoms and are expressed by an identical chemical formula may have different stereostructures, like mirror images. This relationship is called chirality, and the stereostructures have left-handed (labeled L) and right-handed (labeled D) forms. The L and D forms have the same molecular weight and the same binding energy, and their physical properties, such as concentration, melting point, boiling point, refractive index, and thermal conductivity, are also the same. It is difficult to distinguish the stereostructures.

The L and D forms, however, may have totally different biochemical properties, and, from a pharmaceutical or biochemical perspective, it is necessary to determine the absolute configuration of the molecules. The stereostructures are analyzed based on optical rotation, which is a property many chiral molecules generally have.

When the optical rotation is analyzed, right-handed circularly polarized light and left-handed circularly polarized light are radiated onto a sample, and the difference in absorbance is measured. This difference in absorbance is very small in many cases and increases just around the absorption peak of the sample. Therefore, the optical rotation of a sample is generally analyzed around the absorption peak of the sample.

Circular dichroism (CD) spectrometers that measure ultraviolet-visible CD spectra predominated in the past. After development of the technology, vibrational circular dichroism (VCD) spectrometers that measure infrared VCD spectra have been becoming more widespread. In comparison with CD spectra, VCD spectra allow more absorbers to be observed in accordance with the transitions of molecular vibrational states and offer more information.

The method of measuring VCD spectra will now be described. L-form absorbance $A_L$ is measured; D-form absorbance $A_R$ is measured; and the difference $\Delta A$ ($\Delta A = A_L - A_R$) in absorbance is calculated. Then, the ellipticity $\theta$ is obtained as given below:

$$\tan \theta = \Delta A / (A_L + A_R)$$

Next, molecular extinction coefficients ($\epsilon_R$, $\epsilon_L$) are obtained as given below:

$$\theta \cdot 180/\pi \cdot 10 \cdot M/c = 3300(\epsilon_L - \epsilon_R)$$

where M stands for a molecular weight, and c stands for concentration.

When $\epsilon_L - \epsilon_R$ is positive, the elliptically polarized light is right-handed; when $\epsilon_L - \epsilon_R$ is negative, the elliptically polarized light is left-handed.

In the X-Y coordinate system with the vertical axis representing $\Delta A$ or $\epsilon_L - \epsilon_R$ of the L form and the horizontal axis representing the wavelength $\lambda$, a circular dichroism spectrum (CD spectrum) can be plotted. The CD spectra of the L and D forms plotted on the same graph will have symmetrical shapes and different absolute values.

The VCD spectrometer uses a photoelastic modulator (PEM). The PEM includes the piezoelectric element attached to a ZnSe crystal. The ZnSe crystal is distorted by the piezoelectric element to which a voltage applied. Accordingly, birefringence occurs in the ZnSe crystal. When the applied voltage varies with a predetermined frequency, left-handed circularly polarized light and right-handed circularly polarized light can be generated alternately.

PATENT LITERATURE

Patent Literature 1: Japanese Unexamined Patent Application Publication No. 2004-020539

SUMMARY OF THE INVENTION

The PEM can easily convert light in a desired wavelength range to circularly polarized light. When the wavelength range changes, the optical properties of the circularly polarized light also change, and realignment becomes necessary accordingly. In the past, predetermined alignment was applied in accordance with the change in optical properties, and the elements of the VCD spectrometer were set at the same positions.

After long use, the elements in the VCD spectrometer could vary. In some cases, even if the elements are set in their factory-preset states, the polarization status cannot be restored, and desirable CD spectra cannot be obtained. For example, even if identical cells are used, the baseline of the VCD spectra may become uneven because of the individual variability of the cells used for a long time. The individual variability in the elements can also lead to a artifact spectrum, preventing highly symmetrical VCD spectra from being measured.

Accordingly, the circular dichroism spectrometer is required to have an alignment mechanism that adjusts the positions of elements automatically, taking the individual variability among the elements due to changes over time or other reasons into consideration.

The present invention is provided to measure highly symmetrical circular dichroism spectra of L and D forms by cancelling out the individual variability among elements through appropriate alignment and to remove the influence of an uneven baseline by performing preprocessing other than baseline correction. An object of the present invention is to provide a circular dichroism spectrometer having an alignment mechanism that automatically adjusts the elements thereof at appropriate positions.

An alignment mechanism according to the present invention is installed in a VCD spectrometer, to automatically adjust a detector, a detector-side focusing lens for directing the light transmitted through the sample toward the detector, and the like.

An alignment procedure will now be described. The focal position of the detector-side focusing lens is first adjusted (adjustment of the distance between the detector and the detector-side focusing lens, hereafter called position adjustment in the distance direction). The output beams of an interferometer are monitored, and the position and orientation of a fixed mirror of the interferometer are adjusted. Then, the intensity of the output beams is measured to check that the output beams are normal. One reference sample of the D (right-handed) or L (left-handed) form is placed on a sample stage, and the focal position is adjusted through adjustment in the distance direction in each measurement wavelength range. Molecular extinction coefficients ($\epsilon_R$, $\epsilon_L$) of left-handed circularly polarized light and right-handed circularly polarized light are determined, and VCD spectra are obtained. The shapes of the spectra of the D and L forms are compared. The detector-side focusing lens is moved in the direction perpendicular to the light transmitted through the sample (position adjustment in planar direction) and the orientation is adjusted (orientation adjustment), such that the spectra are symmetrical.

The position and orientation of the detector-side focusing lens are adjusted by using a unique characteristic of the VCD spectra that the spectra of the D and L forms are symmetrical.

When a Raman spectrum is measured, the influence of external factors, such as fluorescence, can be reduced by correcting the baseline before peak detection. In comparison with the Raman spectrum, the VCD spectra have an unsteady baseline, and an uneven baseline may cause the peak light of VCD spectrum to have a lower value than the baseline. If the baseline of the VCD spectrum is corrected, peaks would appear in the positive direction and the negative direction and would not be detected accurately. In the present invention, after the VCD spectrum is obtained, a first derivative of the VCD spectrum is obtained to optimize the VCD spectrum so as to make it free of the influence of the baseline.

A circular dichroism spectrometer according to the present invention includes a light source that emits light to be radiated onto a sample, a polarizer that converts light from the light source to linearly polarized light, a photoelastic modulator that converts the linearly polarized light to right-handed circularly polarized light and left-handed circularly polarized light alternately and cyclically, a sample stage on which the sample is placed at a position to which the right-handed circularly polarized light or left-handed circularly polarized light is radiated, a detector-side focusing lens that collects light transmitted through the sample on the sample stage, a detector that detects the light collected by the detector-side focusing lens, a lock-in amplifier that extracts an AC signal in synchronization with a reference signal having the same frequency as the frequency of a voltage applied to the photoelastic modulator, and a spectrum processor that obtains a circular dichroism spectrum on the basis of the AC signal acquired from the lock-in amplifier.

The circular dichroism spectrometer further includes a reference sample positioner that places a reference sample on the sample stage, a focusing-lens position-and-orientation adjustment mechanism that adjusts the position of the detector-side focusing lens in the direction of distance to the sample and in the direction of a plane perpendicular to the light transmitted through the sample and the orientation of the detector-side focusing lens, and a spectrum shape analyzer that obtains a first derivative of the circular dichroism spectrum acquired from the spectrum processor and analyzes the shape. The reference sample positioner places one optical enantiomer, which is either the D form or L form of optical enantiomers, as one reference sample on the sample stage. The spectrum processor obtains a circular dichroism spectrum of the one optical enantiomer, and the spectrum shape analyzer calculates a first derivative of the circular dichroism spectrum of the one optical enantiomer and compares the shape with the shape of the reference spectrum corresponding the one optical enantiomer. The focusing-lens position-and-orientation adjustment mechanism adjusts the position and orientation of the detector-side focusing lens such that the differentiated circular dichroism spectrum of the one optical enantiomer matches the reference spectrum related to the one optical enantiomer.

Then, the reference sample positioner also places the other optical enantiomer on the sample stage. The spectrum processor also obtains a circular dichroism spectrum of the other optical enantiomer, and the spectrum shape analyzer also obtains a first derivative of the circular dichroism spectrum of the other optical enantiomer and compares the shapes of the circular dichroism spectra of the D and L forms. The focusing-lens position-and-orientation adjustment mechanism also adjusts the position and orientation of the detector-side focusing lens such that the circular dichroism spectra of the D and L forms become symmetrical about the wavenumber axis or the wavelength axis.

In another method, reference spectra may be prepared separately for the D and L forms, and the position and orientation of the detector-side focusing lens may be adjusted such that the shapes of the VCD spectra match the shapes of the corresponding reference spectra.

A circular dichroism spectrometer according to the present invention includes a light source that emits light to be radiated onto a sample, a polarizer that converts light from the light source to linearly polarized light, a photoelastic modulator that converts the linearly polarized light to right-handed circularly polarized light and left-handed circularly polarized light alternately and cyclically, a sample stage on which the sample is placed at a position to which the right-handed circularly polarized light or left-handed circularly polarized light is radiated, a detector-side focusing lens that collects light transmitted through the sample on the sample stage, a detector that detects the light collected by the detector-side focusing lens, a lock-in amplifier that extracts an AC signal in synchronization with a reference signal having the same frequency as the frequency of a voltage applied to the photoelastic modulator, and a spectrum processor that obtains a circular dichroism spectrum on the basis of the AC signal acquired from the lock-in amplifier. The circular dichroism spectrometer further includes a reference sample positioner that places a reference sample on the sample stage, a focusing-lens position-and-orientation adjustment mechanism that adjusts the position of the detector-side focusing lens in the direction of the distance to the sample and in the direction of a plane perpendicular to the light transmitted through the sample and the orientation of the detector-side focusing lens, and a spectrum shape analyzer that obtains a first derivative of the circular dichroism spectrum acquired from the spectrum processor and analyzes the shape.

The reference sample positioner places the D form and L form of optical enantiomers in turn, as reference samples on the sample stage. The spectrum processor obtains the circular dichroism spectra of the D and L forms. The spectrum shape analyzer obtains a first derivative of the circular dichroism spectra of the D and L forms separately and compares their shapes with the shapes of the corresponding reference spectra. The focusing-lens position-and-orientation adjustment mechanism adjusts the position and orientation of the detector-side focusing lens such that the differentiated circular dichroism spectra match the corresponding reference spectra.

After the position or orientation of the detector-side focusing lens is adjusted, the optical path also changes. Therefore, it is preferable to adjust the orientation of the detector together with the position or orientation of the detector-side focusing lens. After the position or orientation of the detector-side focusing lens is adjusted, it is advisable to adjust the orientation of the detector such that the intensity of the detector signal is maximized.

It is preferable that a circular dichroism spectrometer according to the present invention further include a detector rotation mechanism which adjusts the orientation of the detector by rotating the detector, and, after the position and orientation of the detector-side focusing lens are adjusted, the detector rotation mechanism rotate the detector and adjust the orientation of the detector such that the intensity of the detector signal is maximized.

When the above-described operation is performed to adjust the position and orientation of the detector-side focusing lens and the orientation of the detector appropriately, the optical positions of the elements are changed. Even if the angle (orientation) of the transmission axis of the polarizer is adjusted before starting alignment, the polarization state may be affected after the alignment. In that case, the orientation of the polarizer needs to be re-adjusted.

A circular dichroism spectrometer according to the present invention may further include a polarizer rotation mechanism that adjusts the orientation of the polarizer, and, after the orientation of the detector is adjusted, the polarizer rotation mechanism may change the orientation θ of the polarizer to adjust the shape of the circular dichroism spectrum of the reference sample.

The adjustment of the orientation of the polarizer need not be based on the CD spectrum as described above and may be achieved with a λ/4 wave plate and an analyzer placed in appropriate positions.

The adjustment procedure will now be described. The λ/4 wave plate and the analyzer are placed between the detector-side focusing lens and the detector. The light polarized by the PEM passes through the λ/4 wave plate. The analyzer is rotated and set at an angle such that the intensity of the AC signal from the detector is maximized. Then, the polarizer is rotated to an orientation θ such that the intensity of the AC signal from the detector is maximized.

The present invention includes a procedure in which the detector-side focusing lens and the detector are adjusted with the alignment mechanism according to the present invention, and then the orientation of the polarizer is set with the conventional method.

When FT-IR analysis is performed, an interferometer may be placed after the light source and may receive light from the light source and output beams onto the sample. With the fixed mirror of the interferometer adjusted in advance, light transmitted through the sample is detected, and the detected signal is supplied to the lock-in amplifier. Then, the lock-in amplifier outputs an AC signal. A VCD spectrum may be obtained from the AC signal.

When an optical filter is further disposed after the interferometer, light outside the wavelength range to be measured can be eliminated. This reduces interference among beams, causing the interferogram to be attenuated slowly. This is preferable because a large time constant can be specified in the lock-in amplifier.

Accordingly, a circular dichroism spectrometer according to the present invention may further include, between the light source and the polarizer, an interferometer that outputs beams, and, between the interferometer and the polarizer, an optical filter that passes circularly polarized light in a desired wavelength range.

The elements of the spectrometer may be free of individual variability initially but may change over years of long use. This change can make the spectrum baseline uneven and can produce a artifact peak.

In the present invention, when the elements are positioned, actual spectra of reference samples of the D and L forms of optical enantiomers are monitored, and the elements are aligned while monitoring the shapes of the spectra. Since the actual spectra of the reference samples are used for alignment, the individual variability of the elements can be considered.

When a VCD spectrum is measured by FT-IR, light in a wide wavelength range enters the PEM. The PEM needs to be adjusted to produce circularly polarized light in a desired wavelength range.

The detector-side focusing lens that collects light transmitted through the sample has chromatic aberration, and the focal distance needs to be adjusted in accordance with the optical properties in each measurement wavelength range.

A detector suited to each wavelength range is used to improve the S/N ratio. If the detector is replaced, optimization becomes necessary. For example, an MCT detector is used in a range of 2000 to 800 $cm^{-1}$, and an InSb detector is used in a range of 4000 to 2000 $cm^{-1}$. Different detectors are used in the ranges divided at 2000 $cm^{-1}$.

The alignment mechanism according to the present invention provides automatic optimization for individual detectors and in individual wavelength ranges, giving a great convenience.

An actually measured VCD spectrum has a distorted base line. If the baseline is corrected, peaks can appear in the negative direction as well as the positive direction. In the present invention, since a first derivative of the VCD spectrum is obtained before it is monitored, the peaks are optimized without being affected by the baseline.

This makes the VCD spectra less likely to be distorted, and highly symmetrical spectra of D and L forms can be obtained.

The auto-alignment mechanism of the conventional interferometer can be used in combination with the present invention.

The position of the fixed mirror of the interferometer is adjusted first by the conventional device, and then, the orientation θ of the polarizer, the position and orientation of the detector-side focusing lens, and the orientation of the detector are adjusted with the alignment mechanism of the present invention. When measurement starts, required elements can be automatically aligned together.

DESCRIPTION OF THE PREFERRED EMBODIMENTS

Figure 1:
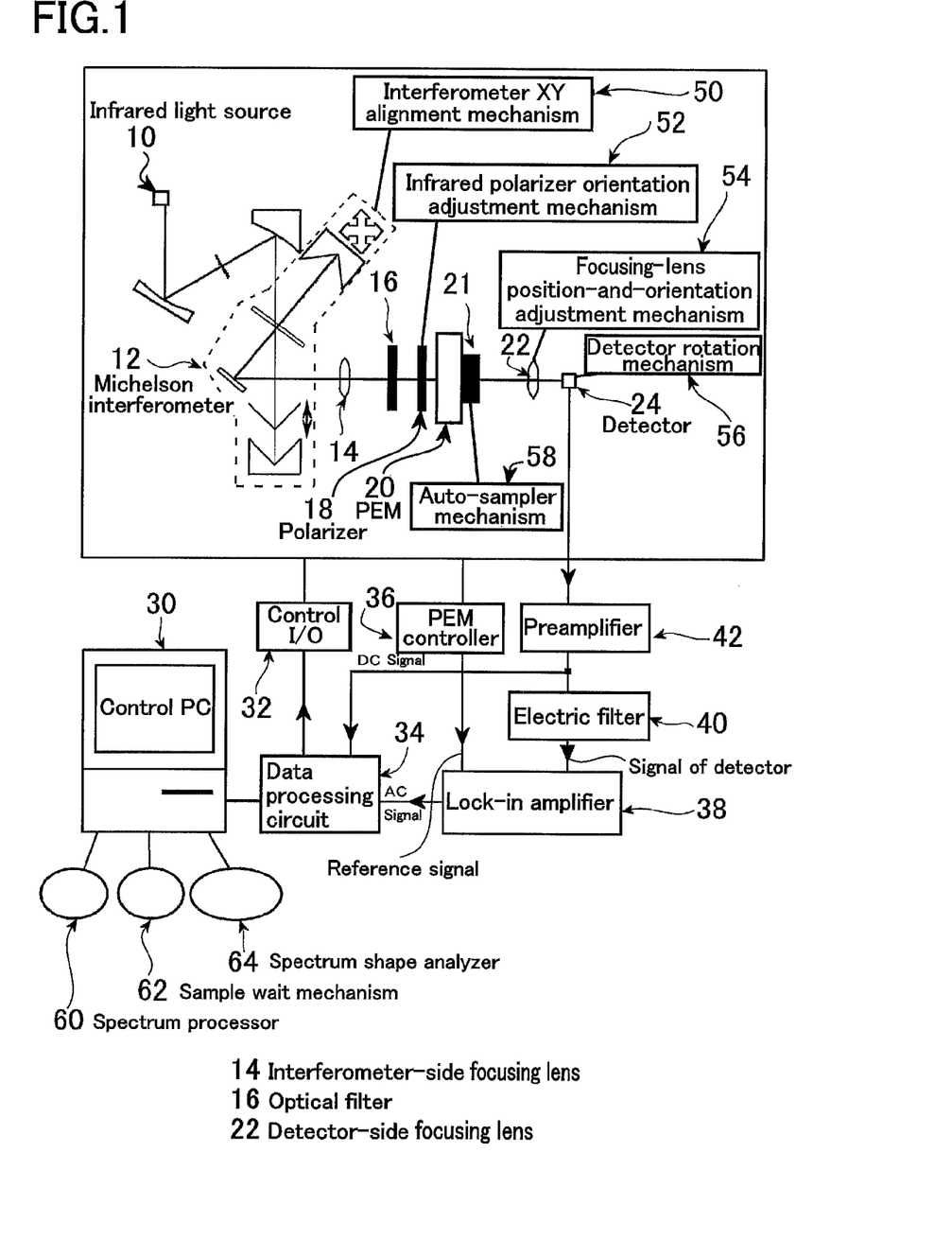
FIG. 1 is a block diagram showing the configuration of an infrared circular dichroism spectrometer having an alignment mechanism according to the present invention.

FIG. 1 shows the configuration of a circular dichroism spectrometer according to the present invention.

The infrared circular dichroism spectrometer includes an infrared light source 10 that emits infrared light, a Michelson interferometer 12 that creates the output beams by the interference of infrared light, an interferometer-side focusing lens 14 that focuses the beams onto a position where a sample is placed, an optical filter 16 that passes light in a predetermined wavelength range, a polarizer 18 that polarizes the beams into linearly polarized light, a photoelastic modulator (PEM) 20 that converts the linearly polarized light to left-handed circularly polarized light and right-handed circularly polarized light alternately and cyclically, a sample stage 21 on which the sample is placed, a detector-side focusing lens 22 that focuses the light transmitted through the sample, and a detector 24 that detects the transmitted light.

If the orientation θ of the polarizer 18 is adjusted, a λ/4 wave plate and an analyzer (not shown in the figure) are placed between the detector-side focusing lens 22 and the detector 24.

The infrared circular dichroism spectrometer further includes the following mechanisms for adjusting the positions and orientations of the elements: An interferometer XY alignment mechanism 50 adjusts the position of the fixed mirror of the Michelson interferometer 12; an infrared polarizer orientation adjustment mechanism 52 adjusts the angle (orientation) θ of the transmission axis of the polarizer 18; a focusing-lens position-and-orientation adjustment mechanism 54 adjusts the position of the focusing lens 22 in the direction of the distance to the detector 24, the position of the focusing lens 22 in the direction of a plane perpendicular to the transmitted beam, and the orientation of the focusing lens 22; and a detector rotation mechanism 56 adjusts the orientation of the detector 24 in accordance with the focal position of the focusing lens.

The sample may be placed by hand or by an auto-sampler mechanism 58. When the orientation θ of the polarizer 18 is adjusted, a λ/4 wave plate and an analyzer need to be placed between the focusing lens 22 and the detector 24. The polarizer 18 should be rotated and set such that the intensity of the CD signal is maximized.

The optical elements in the circular dichroism spectrometer have the following relationship with the adjustment mechanisms.

(1) The focusing-lens position-and-orientation adjustment mechanism 54 adjusts the distance between the detector-side focusing lens 22 and the detector 24 and adjusts the focal position of the focusing lens 22 on the detector 24 in order to detect the light transmitted through the sample.

(2) The interferometer XY alignment mechanism 50 adjusts the position of the fixed mirror of the Michelson interferometer 12 so as to make the center burst position of the beams appropriate.

(3) The λ/4 wave plate and the analyzer (not shown in the figure) are placed between the focusing lens 22 and the detector 24. The infrared polarizer orientation adjustment mechanism 52 rotates the polarizer 18 to an orientation θ where the CD signal is maximized. Polarized light from the PEM 20 is adjusted accordingly.

(4) Separate reference samples of the D and L forms are used. The position and orientation of the focusing lens 22 and the orientation of the detector 24 are adjusted to make the VCD spectra of the D and L forms symmetrical.

Reference samples of the D and L forms are placed on the sample stage 21 one at a time. Left-handed circularly polarized light and right-handed circularly polarized light are directed onto the sample. The focusing-lens position-and-orientation adjustment mechanism 54 adjusts the position and orientation of the focusing lens 22, and then the detector rotation mechanism 56 adjusts the orientation of the detector so that the shapes of the VCD spectra of the D and L forms become symmetrical.

(5) After the position and orientation of the focusing lens 22 and the orientation of the detector 24 are adjusted, polarized light from the PEM 20 may be affected.

In order to improve the state of symmetry of the VCD spectra between optical enantiomers, the orientation θ of the polarizer 18, which has already been adjusted in (3) above, is adjusted here again.

The orientation of the polarizer may be adjusted by using the λ/4 wave plate and the analyzer. The λ/4 wave plate and the analyzer (not shown in the figure) are placed between the focusing lens 22 and the detector 24, and the orientation θ of the polarizer 18 is adjusted again. The intensity of the CD signal is monitored, and the orientation of the analyzer is adjusted to maximize the intensity of the CD signal. Then, the detector 24 monitors the intensity of the CD signal while the infrared polarizer orientation adjustment mechanism 52 is rotating the polarizer 18. The infrared polarizer orientation adjustment mechanism 52 finely adjusts the orientation θ of the polarizer 18 so that the intensity of the CD signal is maximized.

A configuration that extracts a CD signal from the signal of the detector includes an electric filter 40 that removes signals that do not have the frequency of a voltage applied to the PEM 20, a PEM controller 36 that generates a reference signal having the same frequency as the frequency of the voltage applied to the PEM 20, a lock-in amplifier 38 that extracts a signal corresponding to the frequency of the voltage applied to the PEM 20 as an AC signal (interferogram), a data processing circuit 34 that acquires the AC signal and also acquires an infrared absorption spectrum as a DC signal, and a preamplifier 42 that amplifies the signal from the detector 24.

A configuration that controls the elements includes a control PC 30 that performs automatic alignment of the elements and a control I/O 32 that controls the position of the fixed mirror of the Michelson interferometer 12, the position and orientation of the focusing lens 22, and the orientation of the detector 24.

A signal output from the detector 24 is amplified by the preamplifier 42. A signal corresponding to the frequency of the voltage applied to the PEM 20 is extracted by the electric filter 40, and the other signals are eliminated. The electric filter 40 is provided to eliminate unnecessary signals beforehand and to prevent signal saturation from occurring in the lock-in amplifier.

The PEM controller 36 generates the reference signal having the same frequency as the frequency of the voltage applied to the PEM 20. When the detector signal and the reference signal are input to the lock-in amplifier, the control PC 30 adjusts the phase of the reference signal to the phase of the detector signal while monitoring the AC signal supplied from the lock-in amplifier 38. A spectrum processor 60 obtains a VCD spectrum from the AC signal and the DC signal and causes the monitor of the control PC 30 to display the VCD spectrum.

When the position and orientation of the focusing lens 22, the orientation of the detector 24, and the orientation θ of the polarizer 18 are adjusted, a command from the control PC 30 is sent through the control I/O 32 to the adjustment mechanisms of the elements.

The control PC 30 includes the spectrum processor 60, a sample wait mechanism 62, and a spectrum shape analyzer 64.

(1) The spectrum processor 60 receives the AC signal and DC signal acquired by the detector 24 and creates a VCD spectrum.

(2) The sample wait mechanism 62 stops the operation temporarily after the measurement ends until the next reference sample is placed on the sample stage. Each time one reference sample of the D form or L form of optical enantiomers is placed on the sample stage and used to measure a VCD spectrum.

(3) After the reference sample of the D form or L form is placed on the sample stage, the spectrum shape analyzer 64 measures the VCD spectrum. The shape of the VCD spectrum of the reference sample is compared with the shape of the corresponding reference spectrum. If the spectra have different shapes, the control PC 30 issues a command to adjust the positions of the elements, through the control I/O 32. More specifically, when the command reaches the focusing-lens position-and-orientation adjustment mechanism 54 through the control I/O 32, the position and orientation of the focusing lens 22 are adjusted; and, when the command reaches the detector rotation mechanism 56, the orientation of the detector 24 is adjusted.

Figure 2:
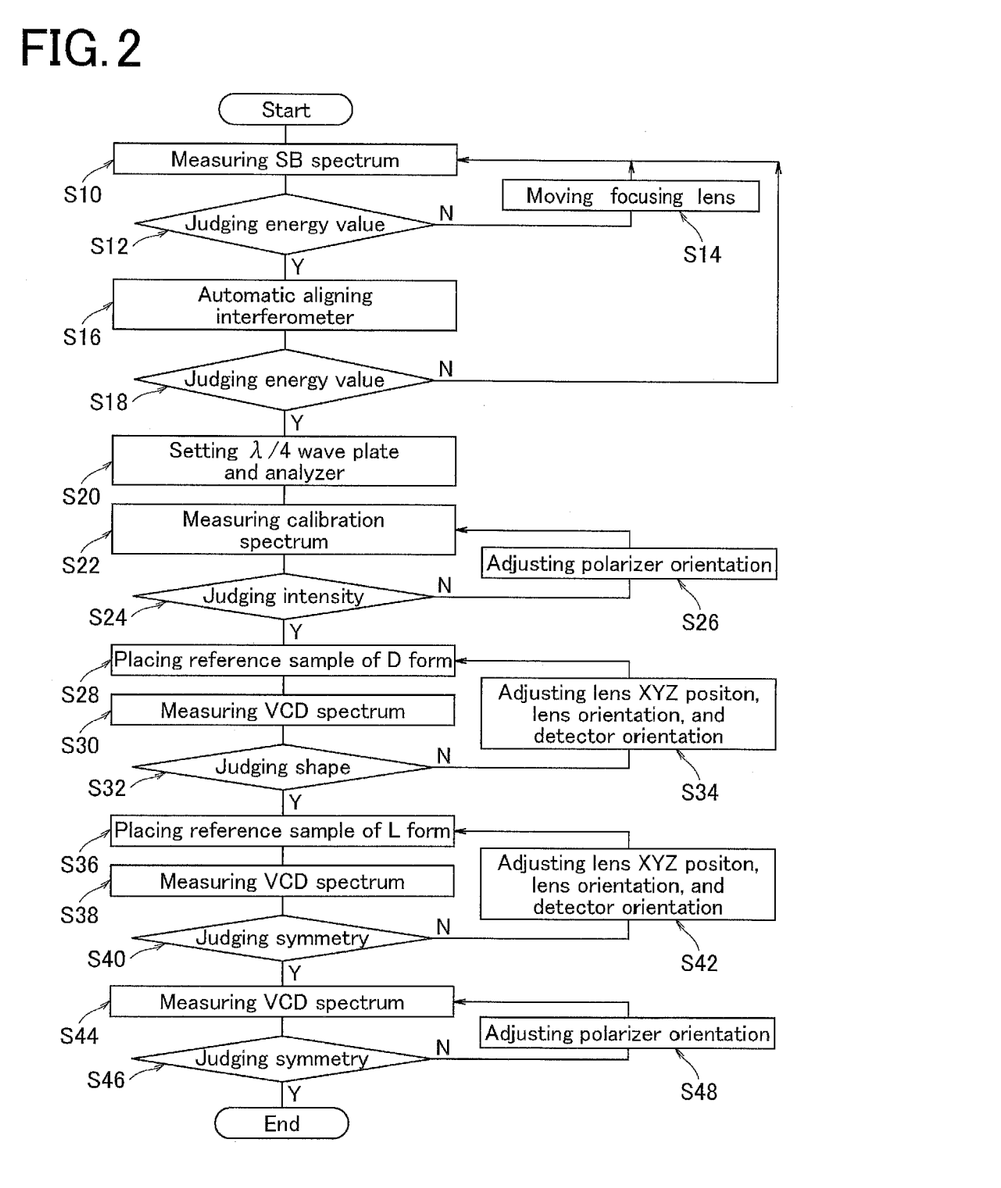
FIG. 2 is a flowchart illustrating the operation of the infrared circular dichroism spectrometer having the alignment mechanism according to the present invention.

FIG. 2 shows a flowchart illustrating the adjustment of optical positions of elements in the spectrometer according to the present invention.

The focal position of the focusing lens 22 is adjusted first. A sample is not placed on the sample stage 21, and the energy value is monitored while the distance between the detector-side focusing lens 22 and the detector 24 is being varied. The focal position of the focusing lens 22 is adjusted such that an appropriate energy value of the detector is obtained (steps S10, S12, S14).

Next, the fixed mirror of the Michelson interferometer 12 is aligned to adjust the output beams. The Michelson interferometer 12 is activated to direct its output beams onto the blank sample (SB), and the beam transmitted through the sample is monitored. The interferometer XY alignment mechanism 50 automatically adjusts the position of the fixed mirror to bring the center burst position of the output beams to an appropriate position (steps S16, S18).

Adjustment of the focal position of the focusing lens 22 and adjustment of the position of the fixed mirror of the Michelson interferometer 12 are repeated until the energy value conditions in the determinations in steps S12 and S18 are satisfied.

Then, a λ/4 wave plate and an analyzer (not shown in the figure) are placed between the focusing lens 22 and the detector 24 (step S20). The PEM 20 is activated while no sample is placed on the sample stage 21, and the intensity of the transmitted beam is monitored while the polarizer 18 is being rotated (step S24). The orientation θ of the polarizer 18 is adjusted to maximize the intensity of the transmitted beam (step S26). Accordingly, the orientation of the polarizer 18 is set to 45°.

The position and orientation of the focusing lens 22 and the orientation of the detector 24 are adjusted next. A reference sample of the D form is placed on the sample stage 21 (step S28), and the VCD spectrum is measured (step S30). In the VCD spectrum measurement, the alignment of the focusing lens 22 is optimized in each measurement wavelength range.

Then, a first derivative of the VCD spectrum is obtained and compared with the reference spectrum, and the shape is judged (step S32). If the first derivative (not shown in the figure) of the VCD spectrum is obtained in advance, an uneven baseline will not cause peaks to appear in the negative direction, and appropriate optimization can be performed. Of course, a corresponding reference spectrum is used.

If the shape of the VCD spectrum differs from the shape of the reference spectrum, the position of the focusing lens 22 in the planar direction and the orientation of the focusing lens 22 are adjusted, and the orientation of the detector 24 is adjusted (step S34). Then, a first derivative of the VCD spectrum is obtained again and compared with the reference spectrum, and the shape is judged (step S32). These steps are repeated until the condition of step S32 is satisfied.

After the condition of step S32 is satisfied, a reference sample of the L form is placed on the sample stage 21 (step S36). The VCD spectrum of the L form is measured in the same way (step S38). The spectra of the L and D forms are compared to see whether they are symmetrical (step S40). If they are not symmetrical, the position of the focusing lens 22 in the planar direction and the orientation of the focusing lens 22 are adjusted, and the orientation of the detector 24 is adjusted (step S42). Then, the VCD spectrum is measured again. These steps are repeated until the condition of step S40 is satisfied.

Instead of the above adjustment of the detector 24 (step S34 and S42), it is preferred that the detector rotation mechanism 56 rotates the detector 24 and adjust the orientation of the detector 24 such that the intensity of the detector signal is maximized, after the position and orientation of the detector-side focusing lens 22 are adjusted.

Instead of checking the symmetry of the VCD spectra, reference spectra of the D and L forms may be prepared, and the focusing lens 22 and detector 24 may be aligned so that the shapes of the actual spectra match the shapes of the corresponding reference spectra.

After the position and orientation of the focusing lens 22 and the orientation of the detector 24 are changed through the steps described above, the current optical alignment differs from that at the end of step S24. If the elements are used in this state, the PEM 20 could produce elliptically polarized light. Therefore, the orientation θ of the polarizer 18 needs to be adjusted again.

The steps of readjusting the orientation θ of the polarizer 18 will be described next. The VCD spectrum of the L form is monitored while the polarizer 18 is being rotated (step S44). It is determined whether the VCD spectrum is symmetrical with the VCD spectrum of the D form (step S46). The orientation θ of the polarizer 18 is adjusted to improve the state of symmetry (step S48).

When the condition of step S46 is satisfied, the alignment of the elements ends.

By using the auto-alignment mechanism of the conventional interferometer in combination with the alignment mechanisms of the present invention, the elements of the circular dichroism spectrometer can be aligned together.

Since the alignment mechanisms of the present invention use the characteristic that the VCD spectra of optical enantiomers are symmetrical, the focusing lens, the detector, and other elements can be aligned automatically while taking account of individual variability caused by aging degradation of the elements.

DESCRIPTION OF REFERENCE NUMBERS

10 . . . light source
12 . . . Michelson interferometer
14 . . . interferometer-side focusing lens
16 . . . optical filter
18 . . . polarizer
20 . . . PEM
21 . . . sample stage
22 . . . detector-side focusing lens
24 . . . detector
30 . . . control PC
32 . . . control I/O
34 . . . data processing circuit
36 . . . PEM controller
38 . . . lock-in amplifier
40 . . . electric filter (e.g. high pass filter)
42 . . . preamplifier
50 . . . interferometer XY alignment mechanism
52 . . . infrared polarizer orientation adjustment mechanism
54 . . . focusing-lens position-and-orientation adjustment mechanism
56 . . . detector rotation mechanism

What is claimed is:

1. A circular dichroism spectrometer including:

a light source that emits light to be radiated onto a sample, a polarizer that converts light from the light source to linearly polarized light, a photoelastic modulator that converts the linearly polarized light to right-handed circularly polarized light and left-handed circularly polarized light alternately and cyclically, a sample stage on which the sample is placed at a position to which the right-handed circularly polarized light or left-handed circularly polarized light is radiated, a detector-side focusing lens that collects light transmitted through the sample on the sample stage, a detector that detects the light collected by the detector-side focusing lens, a lock-in amplifier that extracts an AC signal in synchronization with a reference signal having the same frequency as the frequency of a voltage applied to the photoelastic modulator, a spectrum processor that obtains a circular dichroism spectrum on the basis of the AC signal acquired from the lock-in amplifier, a reference sample positioner that places a reference sample on the sample stage, a focusing-lens position-and-orientation adjustment mechanism that adjusts the position of the detector-side focusing lens in the direction of distance to the sample and in the direction of a plane perpendicular to the light transmitted through the sample and the orientation of the detector-side focusing lens, and a spectrum shape analyzer that obtains a first derivative of the circular dichroism spectrum acquired from the spectrum processor and analyzes the shape, wherein the reference sample positioner places one optical enantiomer, which is either the D form or L form of optical enantiomers, as one reference sample on the sample stage, wherein the spectrum processor obtains a circular dichroism spectrum of the one optical enantiomer, wherein the spectrum shape analyzer calculates a first derivative of the circular dichroism spectrum of the one optical enantiomer and compares the shape with the shape of the reference spectrum corresponding the one optical enantiomer, wherein the focusing-lens position-and-orientation adjustment mechanism adjusts the position and orientation of the detector-side focusing lens such that the differentiated circular dichroism spectrum of the one optical enantiomer matches the reference spectrum related to the one optical enantiomer, wherein the reference sample positioner also places the other optical enantiomer on the sample stage, wherein the spectrum processor also obtains a circular dichroism spectrum of the other optical enantiomer, wherein the spectrum shape analyzer also obtains a first derivative of the circular dichroism spectrum of the other optical enantiomer and compares the shapes of the circular dichroism spectra of the D and L forms, wherein the focusing-lens position-and-orientation adjustment mechanism also adjusts the position and orientation of the detector-side focusing lens such that the circular dichroism spectra of the D and L forms become symmetrical about the wavenumber axis or the wavelength axis.

2. A circular dichroism spectrometer according to claim 1, further including a detector rotation mechanism which adjusts the orientation of the detector by rotating the detector, wherein the detector rotation mechanism rotates the detector and adjust the orientation of the detector such that the intensity of the detector signal is maximized, after the position and orientation of the detector-side focusing lens are adjusted.

3. A circular dichroism spectrometer according to claim 2, further including a polarizer rotation mechanism that adjusts the orientation of the polarizer, Wherein the polarizer rotation mechanism changes the orientation θ of the polarizer to adjust the shape of the circular dichroism spectrum of the reference sample, after the orientation of the detector is adjusted.

4. A circular dichroism spectrometer according to claim 3, further including, an interferometer that outputs beams placed between the light source and the polarizer, and an optical filter that passes circularly polarized light in a desired wavelength range placed between the interferometer and the polarizer.

5. A circular dichroism spectrometer according to claim 2, further including, an interferometer that outputs beams placed between the light source and the polarizer, and an optical filter that passes circularly polarized light in a desired wavelength range placed between the interferometer and the polarizer.

6. A circular dichroism spectrometer according to claim 1, further including, an interferometer that outputs beams placed between the light source and the polarizer, and an optical filter that passes circularly polarized light in a desired wavelength range placed between the interferometer and the polarizer.

7. A circular dichroism spectrometer including:

a light source that emits light to be radiated onto a sample, a polarizer that converts light from the light source to linearly polarized light, a photoelastic modulator that converts the linearly polarized light to right-handed circularly polarized light and left-handed circularly polarized light alternately and cyclically, a sample stage on which the sample is placed at a position to which the right-handed circularly polarized light or left-handed circularly polarized light is radiated, a detector-side focusing lens that collects light transmitted through the sample on the sample stage, a detector that detects the light collected by the detector-side focusing lens, a lock-in amplifier that extracts an AC signal in synchronization with a reference signal having the same frequency as the frequency of a voltage applied to the photoelastic modulator, a spectrum processor that obtains a circular dichroism spectrum on the basis of the AC signal acquired from the lock-in amplifier, a reference sample positioner that places a reference sample on the sample stage, a focusing-lens position-and-orientation adjustment mechanism that adjusts the position of the detector-side focusing lens in the direction of the distance to the sample and in the direction of a plane perpendicular to the light transmitted through the sample and the orientation of the detector-side focusing lens, and a spectrum shape analyzer that obtains a first derivative of the circular dichroism spectrum acquired from the spectrum processor and analyzes the shape, wherein the reference sample positioner places the D form and L form of optical enantiomers in turn, as reference samples on the sample stage, wherein the spectrum processor obtains the circular dichroism spectra of the D and L forms, wherein the spectrum shape analyzer obtains a first derivative of the circular dichroism spectra of the D and L forms separately and compares their shapes with the shapes of the corresponding reference spectra, wherein the focusing-lens position-and-orientation adjustment mechanism adjusts the position and orientation of the detector-side focusing lens such that the differentiated circular dichroism spectra match the corresponding reference spectra.

8. A circular dichroism spectrometer according to claim 7, further including a detector rotation mechanism which adjusts the orientation of the detector by rotating the detector, wherein the detector rotation mechanism rotates the detector and adjust the orientation of the detector such that the intensity of the detector signal is maximized, after the position and orientation of the detector-side focusing lens are adjusted.

9. A circular dichroism spectrometer according to claim 8, further including a polarizer rotation mechanism that adjusts the orientation of the polarizer, Wherein the polarizer rotation mechanism changes the orientation A of the polarizer to adjust the shape of the circular dichroism spectrum of the reference sample, after the orientation of the detector is adjusted.

10. A circular dichroism spectrometer according to claim 9, further including, an interferometer that outputs beams placed between the light source and the polarizer, and an optical filter that passes circularly polarized light in a desired wavelength range placed between the interferometer and the polarizer.

11. A circular dichroism spectrometer according to claim 8, further including, an interferometer that outputs beams placed between the light source and the polarizer, and an optical filter that passes circularly polarized light in a desired wavelength range placed between the interferometer and the polarizer.

12. A circular dichroism spectrometer according to claim 7, further including, an interferometer that outputs beams placed between the light source and the polarizer, and an optical filter that passes circularly polarized light in a desired wavelength range placed between the interferometer and the polarizer.

* * * * *

UNITED STATES PATENT AND TRADEMARK OFFICE
CERTIFICATE OF CORRECTION

PATENT NO.        : 8,749,780 B2
APPLICATION NO.   : 13/851984
DATED             : June 10, 2014
INVENTOR(S)       : Tetsuji Sunami et al.

Page 1 of 1

It is certified that error appears in the above-identified patent and that said Letters Patent is hereby corrected as shown below:

In the Claims:

In Claim 9, column 14, line 2, delete "orientation A" and insert -- orientation $\theta$ --

Signed and Sealed this
Ninth Day of September, 2014

Michelle K. Lee
*Deputy Director of the United States Patent and Trademark Office*